United States Patent
Hopfgartner et al.

(10) Patent No.: US 10,733,787 B2
(45) Date of Patent: Aug. 4, 2020

(54) MODEL-BASED GENERATION AND REPRESENTATION OF THREE-DIMENSIONAL OBJECTS

(71) Applicant: Siemens Healthcare GmbH, Erlangen (DE)

(72) Inventors: Christian Hopfgartner, Fuerth (DE); Felix Lades, Nuenberg (DE); Chris Schwemmer, Forchheim (DE); Michael Suehling, Erlangen (DE); Michael Wels, Bamberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/447,286

(22) Filed: Mar. 2, 2017

(65) Prior Publication Data

US 2017/0270705 A1    Sep. 21, 2017

(30) Foreign Application Priority Data

Mar. 15, 2016 (EP) .................................... 16160475
May 18, 2016 (EP) .................................... 16170187

(51) Int. Cl.
*G06T 15/00* (2011.01)
*G06T 15/08* (2011.01)
(Continued)

(52) U.S. Cl.
CPC .............. *G06T 15/08* (2013.01); *A61B 6/032* (2013.01); *A61B 6/503* (2013.01); *A61B 6/5211* (2013.01);
(Continued)

(58) Field of Classification Search
None
See application file for complete search history.

(56) References Cited

U.S. PATENT DOCUMENTS 5,457,754 A * 10/1995 Han ...................... G06T 7/0012
                                                    382/128
6,778,690 B1 * 8/2004 Ladak ................... G06T 7/0012
                                                    382/131
(Continued)

FOREIGN PATENT DOCUMENTS

DE    102014216702.7    2/2016
GB        2431308 A     4/2007

OTHER PUBLICATIONS

Savchenko V.V., et al.: "Function Representation of Solids Reconstructed from Scattered Surface Points and Contours.", in: Computer Graphics Forum, 1995, pp. 14(4):181-188; 1995;.
(Continued)

*Primary Examiner* — Anh-Tuan V Nguyen
(74) *Attorney, Agent, or Firm* — Harness, Dickey & Pierce, P.L.C.

(57) ABSTRACT

A method for interactively generating a geometric model of a volume object on the basis of three-dimensional image data of an examination region of interest of an examination subject is described. According to an embodiment, a representation of the volume object is determined on the basis of three-dimensional image data and a two-dimensional representation is determined on the basis of the determined representation using a preferably non-linear planar reformation of the three-dimensional object. Subsequently, boundary indicators which define the surface profile of the volume object are edited in the two-dimensional representation. Following the editing, a three-dimensional representation of the edited boundary indicators is generated by back-transforming the edited boundary indicators into three-dimensional space. Finally, a model-based representation of the volume object is generated in three-dimensional space on the basis of the edited boundary indicators. A volume object (Continued)

modeling device is also described. In addition, a medical imaging device is described.

30 Claims, 6 Drawing Sheets

(51) Int. Cl.
| | |
|---|---|
| *G06T 17/20* | (2006.01) |
| *G06T 7/13* | (2017.01) |
| *G06T 19/00* | (2011.01) |
| *A61B 6/03* | (2006.01) |
| *A61B 6/00* | (2006.01) |
| *G06T 15/20* | (2011.01) |

(52) U.S. Cl.
CPC .............. *G06T 7/13* (2017.01); *G06T 15/205* (2013.01); *G06T 17/20* (2013.01); *G06T 19/00* (2013.01); *G06T 2207/30101* (2013.01); *G06T 2207/30172* (2013.01); *G06T 2210/41* (2013.01); *G06T 2215/06* (2013.01)

(56) References Cited

U.S. PATENT DOCUMENTS

| | | | | |
|---|---|---|---|---|
| 7,940,974 B2* | 5/2011 | Skinner | ................ | G06K 9/34 382/131 |
| 8,781,161 B2* | 7/2014 | Kim | ................ | G06K 9/00369 382/103 |
| 2002/0140697 A1* | 10/2002 | Tanibuchi | ................ | G06T 15/20 345/420 |
| 2003/0085890 A1* | 5/2003 | Baumberg | ................ | G06T 15/04 345/420 |
| 2003/0193499 A1* | 10/2003 | Gao | ................ | G06T 17/20 345/420 |
| 2004/0160440 A1* | 8/2004 | Barth | ................ | G06K 9/00201 345/419 |
| 2006/0140473 A1* | 6/2006 | Brooksby | ................ | G01N 21/9515 382/154 |
| 2006/0159326 A1* | 7/2006 | Rasche | ................ | G06T 11/008 382/131 |
| 2006/0228009 A1* | 10/2006 | Fidrich | ................ | G06T 7/12 382/128 |
| 2008/0175463 A1* | 7/2008 | Strommer | ................ | G06K 9/32 382/131 |
| 2008/0262342 A1* | 10/2008 | Averbruch | ................ | A61B 6/12 600/424 |
| 2008/0287796 A1* | 11/2008 | Kiraly | ................ | A61B 5/103 600/443 |
| 2009/0278846 A1* | 11/2009 | Gulsun | ................ | G06T 7/60 345/423 |
| 2009/0322785 A1* | 12/2009 | Lorenz | ................ | G06F 3/04845 345/620 |
| 2010/0131887 A1* | 5/2010 | Salazar-Ferrer | ...... | G06F 3/0481 715/788 |
| 2010/0239140 A1* | 9/2010 | Ruijters | ................ | G06T 19/00 382/130 |
| 2011/0150306 A1* | 6/2011 | Ross | ................ | A61B 6/032 382/131 |
| 2011/0257527 A1* | 10/2011 | Suri | ................ | A61B 8/0858 600/440 |
| 2011/0293162 A1* | 12/2011 | Pajeau | ................ | G06T 5/50 382/132 |
| 2012/0169735 A1* | 7/2012 | Nijlunsing | ............ | G06T 11/001 345/424 |
| 2012/0321162 A1* | 12/2012 | Liu | ................ | G01R 33/443 382/131 |
| 2013/0009958 A1* | 1/2013 | Kitamura | ................ | A61B 6/032 345/424 |
| 2013/0076932 A1* | 3/2013 | Chhibber | ............. | A61B 5/0077 348/222.1 |
| 2013/0121548 A1* | 5/2013 | Kovalan | ................ | G06T 15/08 382/128 |
| 2013/0166256 A1* | 6/2013 | Wirx-Speetjens | ...... | G06F 17/50 703/1 |
| 2013/0195323 A1* | 8/2013 | Liu | ................ | G06T 7/12 382/128 |
| 2013/0216110 A1* | 8/2013 | Zheng | ................ | G06K 9/34 382/128 |
| 2013/0235033 A1* | 9/2013 | Kim | ................ | G06T 17/00 345/419 |
| 2013/0328874 A1* | 12/2013 | Smith-Casem | ......... | G06T 15/30 345/424 |
| 2014/0028672 A1 | 1/2014 | Bang | | |
| 2014/0072191 A1* | 3/2014 | Liang | ................ | G06T 7/0012 382/128 |
| 2014/0198946 A1* | 7/2014 | George | ............. | G01N 29/0609 382/103 |
| 2014/0210821 A1* | 7/2014 | Kapoor | ................ | G06T 15/08 345/424 |
| 2015/0030229 A1* | 1/2015 | Borsdorf | ................ | A61B 6/12 382/132 |
| 2015/0086100 A1* | 3/2015 | Bai | ................ | A61B 8/0891 382/131 |
| 2015/0089365 A1* | 3/2015 | Zhao | ................ | G06F 19/321 715/708 |
| 2015/0138186 A1* | 5/2015 | Carrell | ................ | F24C 15/2021 345/419 |
| 2015/0208039 A1* | 7/2015 | Kuga | ................ | G06T 15/20 348/46 |
| 2015/0212202 A1* | 7/2015 | Mezger | ................ | G01S 17/42 356/4.01 |
| 2015/0253407 A1* | 9/2015 | Nitta | ................ | A61B 5/7425 382/131 |
| 2015/0287194 A1* | 10/2015 | Schoenmeyer | ....... | G06T 7/0012 382/128 |
| 2016/0071318 A1* | 3/2016 | Lee | ................ | G06T 17/00 345/419 |
| 2017/0154435 A1* | 6/2017 | Bitter | ................ | G06T 19/00 |
| 2017/0323443 A1* | 11/2017 | Dhruwdas | ........ | G06K 9/00208 |

OTHER PUBLICATIONS

Zheng Yefeng, et al: "Model-Driven Centerline Extraction for Severely Occluded Major Coronary Arteries", in: Machine Learning in Medical Imaging, LNCS 7588, pp. 10-18, 2012;.

Yang G., et al.: "Automatic Coronary Artery Tree Labeling in Coronary Computed Tomographic Angiography Datasets.", in: Computing in Cardiology, CinC'11, Sep. 2011, pp. 109-112; 2011;.

Sharma P., et al.: "A Parameter Estimation Framework for Patient-Specific Hemodynamic Computations", in: Journal of Computational Physics, Jan. 2015, pp. 281:316-333; 2015;.

Sowell R., et al.: "Volume Viewer. An Interactive Tool for Fitting Surfaces to vol. Data", in: Proceedings of the 6th Eurographics Symposium on Sketch-Based Interfaces and Modeling, pp. 141-148, 2009;.

Carr J.C., et al.:"Reconstruction and Representation of 3D Objects with Radial Basis Functions", in: SIGGRAPH 2001: Proceedings of the 28th annual conference on Computer graphics and interactive techniques, pp. 67-78, 2001;.

Siemens Healthcare GmbH: syngo. CT Coronary Analysis, in: www.healthcare.siemens.de/computed-tomography/options-upgrades/clinical-applicationsisyngo-ct-coronary-analysis, Nov. 12, 2015;.

Sivalingam Udhayaraj, et al.: "Inner and Outer Coronary Vessel Wall Segmentation from CCTA using an Active Contour Model with Machine Learning-based 3D Voxel Context-aware Image Force", in: SPIE Medical Imaging, paper 9785-1, 2016;.

Bajaj C.L., et al.: .Fast Isocontouring for Improved interactivitiy, in: Proceedings of the 1996 Symposium on Volume Visualization, WS '96, Oct. 1996, pp. 39-46; 1996;.

Shape transformation using variational implicit functions Turk el al.; Turk et al.; Shape transformation using variational implicit functions Turk et al.; in: SIGGRAPH '99: Proceedings of the 26th annual conference on Computer graphics and interactive techniques, New York, NY, USA, ACM Press/Addison-Wesley Publishing Co. (1999) 335-442; 1999;.

(56) References Cited

OTHER PUBLICATIONS

Kretschmer Jan, et al.: "Interactive Patient-Specific Vascular Modeling with Sweep Surfaces", in: IEEE Transactions on Visualization and Computer Graphics, vol. 19, Iss. 12, pp. 2828-2837, Dec. 2013;.
Ricci A.: "A constructive geometry for computer graphics", in: The Computer Journal, vol. 16, No. 2. pp. 157-160. 1973;.
Kirişli H., et al.: "Standardized evaluation framework for evaluating coronary artery stenosis detection, stenosis quantification and lumen segmentation algorithms in Computer Tomography Angiography.", in: Medical Image Analysis, Dec. 2013, pp. 17(8):1-18; 2013;.
Zheng Yefeng: "Robust and Accurate Coronary Artery Centerline Extraction in CTA by Combining Model-Driven and Data-Driven Approaches" Advances in Communication Networking : 20th Eunice/IFIP EG 6.2, 6.6 International Workshop, Rennes, France, Sep. 1-5, 2014, Revised Selected Papers; [Lecture Notes in Computer Science, ISSN 1611-3349], Springer Verlag, DE, p. 74-81, XP047042220; 2013;.
Lugauer F., et al.: "Precise Lumen Segmentation in Coronary Computed Tomography Angiography.", in: Medical Computer Vision: Algorithms for Big Data, MCV '14, Sep. 2014, pp. 137-147; 2014;.
Morse B.S., et al.: "Interpolating Implicit Surfaces from Scattered Surface Data Using Compactly Supported Radial Basis Functions.", in: International Conference on Shape Modeling and Applications, SMI '01, May 2001, pp. 89-98; 2001;.
Wels, M. et al., "Intuitive and Accurate Patient-Specific Coronary Tree Modeling from Cardiac Computer-Tomography Angiography," Mar. 15, 2016.
Siemens Healthcare GmbH: syngo. CT Coronary Analysis, in: www.healthcare.siemens.de/computed-tomography/options-upgrades/clinical-applications/syngo-ct-coronary-analysis, Feb. 18, 2016;.
Diepenbrock, S. et al.: "From imprecise user input to precise vessel segmentations"; in Eurographics Workshop on Visual Computing for Biology and Medicine; pp. 65-72; XP002776205 ; 2012.
Joaquim, Peiró et al.: "Automate reconstruction of a patient-specific high-order surface representation and its application to mesh generation for CFD calculations"; in: Medical & Biological Engineering & Computing; vol. 46, No. 11; pp. 1069-1083; XP019864864; ISSN: 1741-0444; DOI: 10.1007/S11517-008-0390-3; 2008.
Wong, Wilbur C. K. et al.: "Probabilistic vessel axis tracing and its application to vessel segmentation with stream surfaces and minimum cost paths"; in: Medical Image Analysis; vol. 11, No. 6; pp. 567-587, XP822318283; ISSN: 1361-8415, DOI: 18.1016/J.MEDIA.2887.85.883; 2007.
Morse, Bryan S. et al.: "Interpolating implicit surfaces from scattered surface data using compactly supported radial basis functions"; pp. 78-87; XP058318111; DOI: 10.1145/1198555.1198645; 2005.
Kanitsar A. et al: "CPR-Curved Planar Reformation"; IEEE Visualization 2002; Proceedings; Boston; MA, Oct. 27-Nov. 1, 2002; [Annual IEEE Conference on Visualization], New York, NY: IEEE; US; pp. 37-44; XP058097035; ISBN: 978-0/7803-7498-0;.
Buehler et al; "Geometric Methods for Vessel Visualization and Quantification—A Survey"; Internet Citation; No. 35; pp. 1-24; XP002482268;.
Guanyu Yang et al: "Automatic centerline extraction of coronary arteries in coronary computed tomographic angiography"; The International Journal of Cardiovascular Imaging; XP055016051; ISSN: 1569-5794, DOI:10.1007/510554-011-9894-2;.
Velut J et al: "Assessment of qualitative and quantitative features in coronary artery MRA"; IRBM; Elsevier; Amsterdam; NL; Bd. 32; Nr. 4; Seiten 229-242; XP028389843; ISSN: 1959-0318; DOI: 0.1016/J.IRBM.2011.05.002;.

* cited by examiner

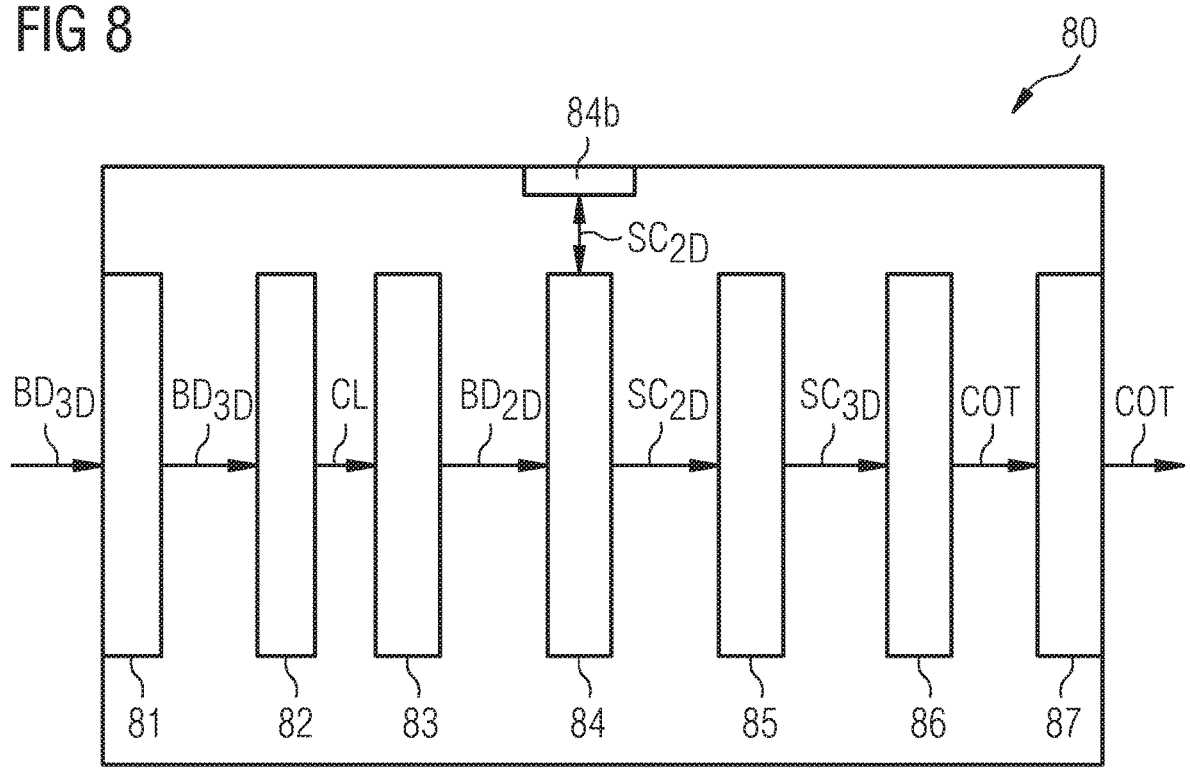

MODEL-BASED GENERATION AND REPRESENTATION OF THREE-DIMENSIONAL OBJECTS

PRIORITY STATEMENT

The present application hereby claims priority under 35 U.S.C. § 119 to European patent application numbers EP 16160475.6 filed Mar. 15, 2016 and EP 16170187.5 filed May 18, 2016, the entire contents of each of which are hereby incorporated herein by reference.

FIELD

At least one embodiment of the invention generally relates to a method for the interactive generation and modification of a geometric model of a volume object on the basis of three-dimensional image data of an examination region of interest of an examination subject. At least one embodiment of the invention further generally relates to a volume object modeling device. Finally, at least one embodiment of the invention also generally relates to a medical imaging device.

BACKGROUND

Two- or three-dimensional image data, which may be used for visualizing an imaged examination subject and in addition for further applications, is frequently generated with the aid of modern imaging methods.

In three-dimensional medical imaging, it is often necessary to represent three-dimensional image data or, as the case may be, volumetric geometric structures present in the image data in a suitable way with the aid of a geometric model in order to enable measurements to be taken or to conduct a diagnostic analysis at a higher level. This procedure is referred to in the following also as "volume object modeling".

Examples of such more complex approaches for diagnostic purposes are the simulation of the blood flow through the coronary vessels of the heart by modeling the fluid dynamics and the examination of plaque deposits in cases of arteriosclerosis. In order to be able to carry out these investigations it is necessary to translate the measurement signals or measurement data into a meaningful geometric semantic system relating to the imaged structures. Toward that end, methods for segmenting acquired medical images have been developed with the aid of which an image volume is divided up into known objects either in an automated manner or interactively. Unfortunately, fully automatic methods are often extremely prone to errors and for that reason must be supplemented by suitable interactive methods in order to achieve an additional "refinement" of the automatically determined segments and geometric model structures associated therewith.

In an example application, the entire vascular structure of the coronary tree perfused by the blood is modeled interactively on the basis of image data obtained through cardiac computed-tomography angiography (CCTA). Existing interactive methods from the prior art are not very user-friendly and typically are limited to linear planar two-dimensional representations of the actual 3D data, such as, for example, to representations which have been obtained by way of a multiplanar reformation perpendicularly to the centerlines of the vessels. Within the framework of these interactive modeling techniques, surface markings, such as open or closed aggregations of surface points, for example, are edited or marked in order to be used for a subsequent segmentation.

The multiplanar reformation comprises sections of the three-dimensional data in which the editing is carried out. In most cases, however, the course of the individual vessels is not consistent with these sections, with the result that an editing operation based on these sections is incomplete and may easily lead to incorrect results.

SUMMARY

An embodiment of the present invention is directed to an interactive method for modeling volume objects, in particular vascular structures, which enables a more precise and easier editing of surface structures for a subsequent segmentation and model-based representation of the volume objects.

An embodiment of the present invention is directed to a method for interactively generating a geometric model of a volume object; an embodiment of the present invention is directed to a volume object modeling device; and an embodiment of the present invention is directed to a medical imaging device.

In an embodiment of the inventive method for the interactive generation of a geometric model of a volume object on the basis of three-dimensional image data of an examination region of interest of an examination subject, a representation of the volume object is first determined on the basis of three-dimensional image data. The image data of the volume object may have been acquired for example using a computed tomography or a magnetic resonance tomography system, i.e. the data is ultimately measurement data of the tomography systems or image data reconstructed therefrom. The image data therefore comprises three-dimensional image data or a set of two-dimensional slice data that covers a three-dimensional volume. Particularly preferably, the three-dimensional image data is medical image data which has been obtained from a patient.

The volume object modeling device according to an embodiment of the invention has a representation determination unit for determining a representation of a volume object on the basis of three-dimensional image data. Also part of the inventive volume object modeling device of at least one embodiment is a reformation unit for generating a two-dimensional representation using a preferably non-linear planar reformation of the volume object on the basis of the determined representation.

An embodiment of the inventive volume object modeling device additionally comprises an image evidence editing unit for editing boundary indicators which define the actual surface profile of the volume object in the two-dimensional representation. In addition, the inventive volume object modeling device has a back-transformation unit which is configured for generating a three-dimensional representation of the edited boundary indicators by back-transformation of the edited boundary indicators into three-dimensional space. Furthermore, the inventive volume object modeling device comprises a modeling unit which is configured to model the volume object in three-dimensional space on the basis of the edited boundary indicators or, as the case may be, to generate a model-based representation of the volume object.

An embodiment of the inventive medical imaging device, preferably a CT system, has a scan unit for scanning an examination region of interest of a subject that is to be examined, a control device for controlling the scan unit, and an embodiment of an inventive volume object modeling device.

The majority of the essential components of the volume object modeling device according to at least one embodiment of the invention may be embodied in the form of software components. This relates in particular to the representation determination unit, the reformation unit, the image evidence editing unit, the back-transformation unit and the modeling unit. In principle, however, some of these components may also be realized in the form of software-assisted hardware, for example FPGAs or the like, in particular when particularly fast calculations are involved. Equally, the required interfaces may be embodied as software interfaces, for example when it is simply a question of importing data from other software components. However, they may also be embodied as hardware-based interfaces which are controlled by suitable software.

A substantially software-based implementation has the advantage that control devices of medical imaging devices already used previously in the prior art can also be easily upgraded via a software update in order to operate in the manner according to an embodiment of the invention. In that respect, at least one embodiment is directed to a corresponding computer program product having a computer program which can be loaded directly into a memory device of a control device of a medical imaging device and having program sections for carrying out all steps of the method according to the invention when the program is executed in the control device. As well as the computer program, such a computer program product may possibly comprise additional constituent parts such as e.g. documentation and/or additional components, including hardware components, such as e.g. hardware keys (dongles, etc.) to allow the software to be used.

A computer-readable medium, for example a memory stick, a hard disk or some other transportable or permanently installed data carrier, on which the program sections of the computer program that can be read in and executed by a computer unit of the control device are stored, may be used for transporting the computer program to the control device and/or for storing the same on or in the control device. For this purpose, the computer unit may have e.g. one or more cooperating microprocessors or the like.

BRIEF DESCRIPTION OF THE DRAWINGS

The invention is explained once again below in more detail with the aid of example embodiments and with reference to the attached figures, in which:

FIG. 8 shows a block diagram by way of which a volume object modeling device according to an example embodiment of the invention is illustrated.

DETAILED DESCRIPTION OF THE EXAMPLE EMBODIMENTS

Figure 1:
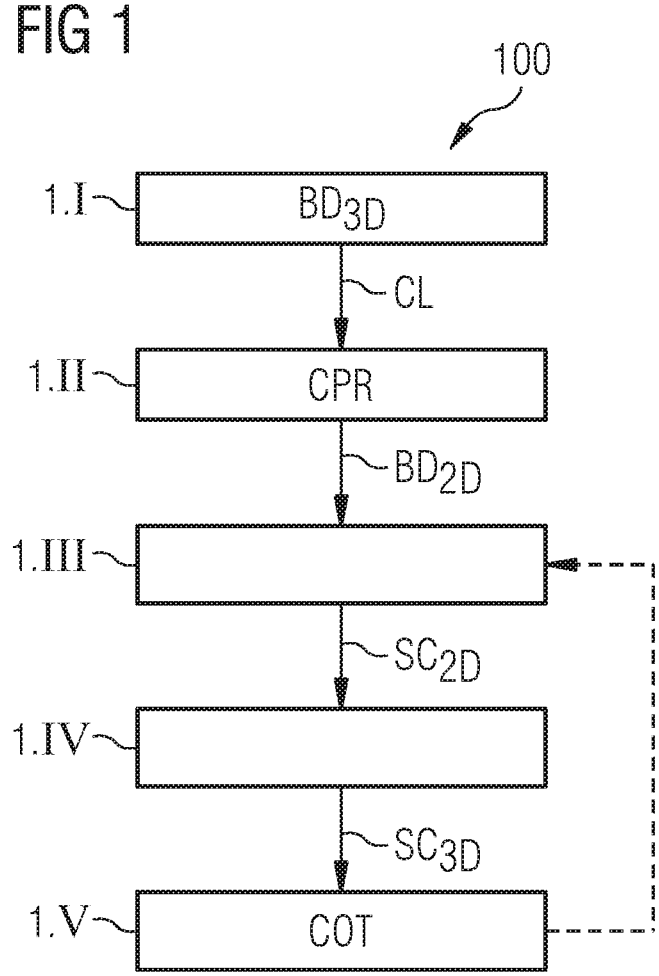
FIG. 1 shows a flowchart which illustrates a method for the interactive geometric modeling of a volume object on the basis of three-dimensional image data of an examination region of interest of an examination subject.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

An embodiment of the present invention is directed to a method for interactively generating a geometric model of a volume object; an embodiment of the present invention is directed to a volume object modeling device; and an embodiment of the present invention is directed to a medical imaging device.

In an embodiment of the inventive method for the interactive generation of a geometric model of a volume object on the basis of three-dimensional image data of an examination region of interest of an examination subject, a representation of the volume object is first determined on the basis of three-dimensional image data. The image data of the volume object may have been acquired for example using a computed tomography or a magnetic resonance tomography system, i.e. the data is ultimately measurement data of the tomography systems or image data reconstructed therefrom. The image data therefore comprises three-dimensional image data or a set of two-dimensional slice data that covers a three-dimensional volume. Particularly preferably, the three-dimensional image data is medical image data which has been obtained from a patient.

The image data and/or the representation may also be sourced from a database. This means that the image data or the representation has already been acquired or determined in advance, is present in the database and is simply obtained, i.e. retrieved, via an input interface.

What is to be understood by a representation of the volume object is a dataset which in some way or other replicates the geometric structure of the volume object or, as the case may be, the position and the course of the volume object, possibly also only at certain selected positions or in sections. An example thereof is a line tracing the course of a hollow organ and in particular the centerline representation that will be explained later. In principle, however, the representation may also be the measured, unmodified or edited (e.g. filtered) image data itself.

Furthermore, a two-dimensional representation using a preferably non-linear planar reformation of the three-dimensional object is generated on the basis of the determined representation. What is to be understood as a non-linear planar reformation is an image which diverges from a pure representation of individual planes or linear sections of the three-dimensional image data, such as are used in multiplanar reformation (MPR). In non-linear planar reformation, therefore, image elements or pixels which do not all lie in one plane are imaged two-dimensionally. One type of non-linear planar reformation is curvilinear or curved planar reformation, also abbreviated as CPR (CPR=curved planar reformation). This enables representations of datasets which are defined by way of individual geometric centerlines or complex centerline graphs. CPRs are conventionally applied in the visualization of vessels, since the generated sections permit a careful examination of the lumen of the vessels and include valuable anatomical context.

Alternatively, a reformatting method as described in DE 10 2014 216 702.7, the entire contents of which are hereby incorporated herein by reference, may also be applied. In this case a three-dimensional parameterized surface is specified which is congruent with an anatomical structure of a three-dimensional object that is to be examined. The three-dimensional parameterized surface is subsequently mapped onto a two-dimensional parameterized surface. Finally, the three-dimensional object that is to be examined is represented two-dimensionally by mapping pixels assigned to the three-dimensional parameterized surface onto the two-dimensional parameterized surface.

ARAP optimization methods may find application in the determination and optimization of the two-dimensional parameterized surface. In contrast to conventional methods, however, a surface exactly fitted to the anatomy serves as an initial surface.

With this particular method, the reformation of the regions that are to be examined is determined to a great extent by the anatomy of objects to be examined that are also very different. For example, complex and extensive structures such as bone skeletons, for example, may be acquired and represented in such a way that they can be examined quickly. The mentioned three-dimensional parameterized surface may be parameterized both continuously and discretely.

In the two-dimensional representation, boundary indicators which define the surface profile of the volume object are edited, for example by the user, who draws in corresponding marking lines in the two-dimensional representation which simulate the contours or boundaries or demarcation lines of the volume object. The boundary indicators may be drawn in on the basis of so-called image evidence cues, i.e. structures in the image which may be used for the segmentation. However, the boundary indicators may also be drawn in, insofar as the image evidence cues are absent from the acquired 3D image data or the reformatted two-dimensional image data, taking into consideration the anatomical knowledge of the user. The marking lines may also be edited or drawn in automatically in the first instance within the editing program on the basis of the three-dimensional image data and the representation.

For example, the automatically determined boundary indicators may be displayed to the user as marking lines in the two-dimensional representation. If the user agrees with the determined boundary indicators, the method may be continued in an automated manner. If, however, the user wishes to make changes to the drawn-in boundary indicators, he or she draws these in for example as marking lines in the two-dimensional representation. This process can be made even easier if the user is able to move the automatically calculated marking lines of the boundary indicators displayed to him or her in the two-dimensional representation, for example on a display as an image presentation device, and change their shape, in particular distort, stretch, compress, rotate them, etc. With this partially automated editing, a more precise definition of the initially automatically provided boundary indicators is achieved by way of an intervention on the part of the user.

Subsequently, a three-dimensional representation of the edited boundary indicators is generated by back-transformation of the edited boundary indicators into three-dimensional space. In the back-transformation, an algorithm is applied which is inverse to the algorithm used in the step of generating a two-dimensional image representation. In other words, a successive execution of the reformation and the operation inverse thereto produces the starting image. Since, however, the back-transformation was applied to the marking lines, these are now transferred into three-dimensional space, where they represent sampling points for a subsequent modeling of the volume object.

Finally, a modeled or model-based representation of the volume object is generated in three-dimensional space on the basis of the edited boundary indicators. For example, information relating to the shape of the boundaries of the volume object that is to be represented is incorporated in the determination of such a model-based representation. This may be, for example, information relating to the geometric shape of the cross-section of the volume object. The shape of the wanted volume object can then be reconstructed in combination with the determined marking lines as sampling points.

A method for modeling a volume object on the basis of existing marking lines is described for example in Carr, J. C., Beatson, R. K., Cherrie, J. B., Mitchell, T. J., Fright, W. R., McCallum, B. C, and Evans, T. R.: "Reconstruction and Representation of 3D Objects with Radial Basis Functions", in: SIGGRAPH 2001: Proceedings of the 28th annual conference on computer graphics and interactive techniques, pages 67-76, 2001, the entire contents of which are hereby incorporated herein by reference. In this case an implicit modeling of a volume object is achieved by interpolation of its surface by way of variational interpolation of radial basis functions in three-dimensional space.

By way of the method according to an embodiment of the invention it is made possible for users to make annotations in image data, in particular for the purpose of segmenting volume objects, interactively and highly intuitively in a two-dimensional representation, which in spite of the missing third dimension fully comprise indicators defining the shape of the volume objects. The user is able to draw in the marking lines completely in one or two image representations and as a result of the reformatted representation obtains a general overview of the course of the marking lines. Subsequently, an automated transformation of the annotations into three-dimensional space enables the annotations to be used directly for the modeling of the volume object, without the need for the user him- or herself to initiate a transfer of his or her annotations into the three-dimensional space.

In this way the user is provided with a tool for the seamless editing of marking lines or boundary indicators. The transformation steps as well as the modeling step of the method can be accomplished with relatively little computational overhead, with the result that the user is provided with an interactive method with a visualization that is available virtually in real time as feedback or as a view for verification and control purposes. The progress of the method is transparent and easy to monitor since intermediate results of the method can be displayed to the user with only a short delay.

The volume object modeling device according to an embodiment of the invention has a representation determination unit for determining a representation of a volume object on the basis of three-dimensional image data. Also part of the inventive volume object modeling device of at least one embodiment is a reformation unit for generating a two-dimensional representation using a preferably non-linear planar reformation of the volume object on the basis of the determined representation.

An embodiment of the inventive volume object modeling device additionally comprises an image evidence editing unit for editing boundary indicators which define the actual surface profile of the volume object in the two-dimensional representation. In addition, the inventive volume object modeling device has a back-transformation unit which is configured for generating a three-dimensional representation of the edited boundary indicators by back-transformation of the edited boundary indicators into three-dimensional space. Furthermore, the inventive volume object modeling device comprises a modeling unit which is configured to model the volume object in three-dimensional space on the basis of the edited boundary indicators or, as the case may be, to generate a model-based representation of the volume object.

An embodiment of the inventive medical imaging device, preferably a CT system, has a scan unit for scanning an examination region of interest of a subject that is to be examined, a control device for controlling the scan unit, and an embodiment of an inventive volume object modeling device.

Implementing an embodiment of the invention in a CT system has the advantages that the scan duration of a CT system is relatively short. It amounts to only a few seconds, compared to scanning with MR systems, which may require several minutes. This is particularly advantageous in the case of the examination of emergency patients, for whom any time delay may be life-threatening. Furthermore, CT systems are more widely available and less expensive than MR systems.

The medical imaging device according to an embodiment of the invention may also comprise an MR system.

On the other hand, MR systems have the advantage that an examination conducted with them involves no exposure to x-ray radiation and the soft part contrast of an image acquired via an MR system is improved in comparison with a CT system.

The majority of the essential components of the volume object modeling device according to at least one embodiment of the invention may be embodied in the form of software components. This relates in particular to the representation determination unit, the reformation unit, the image evidence editing unit, the back-transformation unit and the modeling unit. In principle, however, some of these components may also be realized in the form of software-assisted hardware, for example FPGAs or the like, in particular when particularly fast calculations are involved. Equally, the required interfaces may be embodied as software interfaces, for example when it is simply a question of importing data from other software components. However, they may also be embodied as hardware-based interfaces which are controlled by suitable software.

A substantially software-based implementation has the advantage that control devices of medical imaging devices already used previously in the prior art can also be easily upgraded via a software update in order to operate in the manner according to an embodiment of the invention. In that respect, at least one embodiment is directed to a corresponding computer program product having a computer program which can be loaded directly into a memory device of a control device of a medical imaging device and having program sections for carrying out all steps of the method according to the invention when the program is executed in the control device. As well as the computer program, such a computer program product may possibly comprise additional constituent parts such as e.g. documentation and/or additional components, including hardware components, such as e.g. hardware keys (dongles, etc.) to allow the software to be used.

A computer-readable medium, for example a memory stick, a hard disk or some other transportable or permanently installed data carrier, on which the program sections of the computer program that can be read in and executed by a computer unit of the control device are stored, may be used for transporting the computer program to the control device and/or for storing the same on or in the control device. For this purpose, the computer unit may have e.g. one or more cooperating microprocessors or the like.

The dependent claims as well as the following description in each case contain particularly advantageous embodiments and developments of the invention. In this regard, in particular the claims of one claims category may also be developed analogously to the dependent claims of a different claims category. Furthermore, the various features of different example embodiments and claims may also be combined within the scope of the invention in order to create new example embodiments.

In one embodiment of the inventive method for interactively generating a geometric model of a volume object on the basis of three-dimensional image data of an examination region of interest of an examination subject, the volume object has a tubular structure. Such a tubular structure may for example comprise a three-dimensional vascular structure, preferably a coronary vascular structure. Widely branched fine vascular structures of the type are difficult to model solely in an automated manner on the basis of three-dimensional image data. In particular when blood flow calculations are to be performed, it is, however, very important that the vessels represented in model form are fluid-tight and are reconstructed reasonably exactly.

With the method according to an embodiment of the invention, the advantages of an automated modeling of such vascular structures are combined with the possibilities of a correcting intervention on the part of the user, such that a more precise result is achieved than in the case of a strictly manual or strictly automated approach.

In a particularly effective variant of the method according to an embodiment of the invention, the representation comprises a central path, also known as a centerline, along the course of the tubular structure. It represents, at least approximately, the course of the hollow organ in question. The centerline may be determined for example manually by a user and/or automatically by way of an extraction algorithm. A semiautomatic, i.e. an automatic, but user-assisted, determination is also possible. A method of determining such a centerline in a vascular structure is described in Zheng, Y., Shen, J., Tek, H., Funka-Lea, G.: "Model-Driven Centerline Extraction for Severely Occluded Major Coronary Arteries", in: Machine Learning in Medical Imaging, LNCS 7588, pages 10-18, 2012, the entire contents of which are hereby incorporated herein by reference. Since the centerline replicates the course of the tubular structures in three-dimensional space, it can be used in order to specify a surface in three-dimensional space for the subsequent reformation, which surface also comprises the tube walls in their course along the centerline. In this way, a seamless tracking of the tube walls in the reformatted two-dimensional representation is made possible which facilitates the localization and annotation of the tube walls.

In an alternative variant embodiment of the inventive method, the edited boundary indicators mark the course of the tube walls of the tubular structure. In other words, the marking lines mark the course of the tube walls and in this way define the limits of a hollow volume that is to be determined in a subsequent examination, albeit initially still in two-dimensional space.

In a particularly effective embodiment of the inventive method, the back-transformation of the marked two-dimensional representation into three-dimensional space is based on an inversion of the non-linear planar reformation. Since the modeling of the volume object must take place in three-dimensional space, the edited annotations are back-transformed into the three-dimensional space once again by inversion of the preceding reformation. Because the back-transformation is equivalent to an inversion of the preceding reformation, it is ensured that the marking lines or, as the case may be, the edited boundary indicators are consistent in terms of shape with the actual structural makeup of the volume object. Accordingly, a precise and accurate modeling of the volume object that is to be examined is achieved.

In a variant of the method according to an embodiment of the invention, contradictory boundary indicators that were drawn in earlier in the three-dimensional representation of the edited boundary indicators and extend through a predetermined volume region around a currently drawn-in marking line are discarded. This approach may be implemented for example in the case of the examination of a hollow organ or tube-shaped object to the effect that older marking lines or boundary indicators lying around a new marking line in a volume region which is arranged by way of a stack composed of circular ring segments around the centerline of the hollow organ at a predetermined angle and at a predetermined distance from the centerline, are discarded. In this way, incorrectly or inaccurately annotated marking lines are replaced by more precisely drawn marking lines, wherein a gradual convergence to an optimum, insofar as the precision of the marking lines is concerned, is achieved as a consequence of the iteration.

In concrete terms, this means that the steps of editing the boundary indicators and discarding contradictory boundary indicators or marking lines are performed alternately in an iterative process until all of the boundary indicators have been edited and all the contradictory boundary indicators have been eliminated. With this variant, a stepwise refinement of the drawn-in annotations or marking lines takes place, wherein older marking lines that "get in the way of" or come too close to currently drawn-in marking lines are discarded.

Preferably, the modeling of the volume object on the basis of the edited boundary indicators comprises an implicit modeling by interpolating the surfaces of the volume object with radial basis functions, wherein so-called implicit surfaces are defined. Implicit surfaces permit a very flexible, "model-free" modeling of boundaries without restriction to specific basic shapes of the boundaries. Consequently, an increased flexibility and accuracy in the determination of the boundaries of a volume object are achieved.

Particularly preferably, the modeled volume object is represented pictorially by way of a surface network in three-dimensional space and/or by way of intersection lines lying in the reformatted surface of the two-dimensional representation. In the case of the latter form of representation, the user observes a reformatted surface following the course of the volume object and a linear representation or intersection line representation of the modeled boundaries of the volume object that intersect the reformatted surface. The intersection line representation is produced as a result of the curved surface following the course of the volume object intersecting implicit surfaces of the volume object generated in model form, which implicit surfaces are imaged in this variant in a two-dimensional representation as intersection lines.

For the case of a visualization with intersection line representation, the intersection lines may be used as candidate boundary indicators for the purpose of refining the model in a repeated step of editing boundary indicators performed within the scope of an iteration. In other words, the determined volume object itself may be used again in its projection representation as marking lines in the two-dimensional representation, which can then be subsequently corrected by the user in the two-dimensional representation in order thereby to achieve an improvement in the accuracy of the determination of the boundaries of the volume object.

FIG. 1 shows a flowchart 100 which illustrates a method for the interactive geometric modeling of a volume object on the basis of three-dimensional image data of an examination region of interest of an examination subject according to an example embodiment of the invention. The method entails the modeling of vascular structures of a coronary tree which may subsequently be used for different types of calculations for diagnostic purposes, relating for example to the blood flow through the vessels. The method described by way of the flowchart in FIG. 1 is additionally explained with the aid of FIG. 2 to FIG. 7, in which illustrations pertaining to the individual method steps are shown which demonstrate the individual steps in detail.

At step 1.I, three-dimensional data $BD_{3D}$ is initially received which originates for example from a cardiac CT angiography (CTA) scan. In order to be able to carry out quantitative investigations in respect of the proper functioning of the coronary systems on the basis of the data $BD_{3D}$, it is necessary to segment the image data. For example, it is possible by this to demarcate the vessels from their environment and thus determine for example a volume and cross-sections of the vascular system, and from this to calculate a maximum flow rate through the vascular system. The first action in step 1.I is to specify a centerline CL of the vessels in the image data $BD_{3D}$. The centerline or central path CL may be understood as a representation of the vascular structures. It determines the course of the path of the vascular structures that are recorded in the image data $BD_{3D}$.

Figure 2:
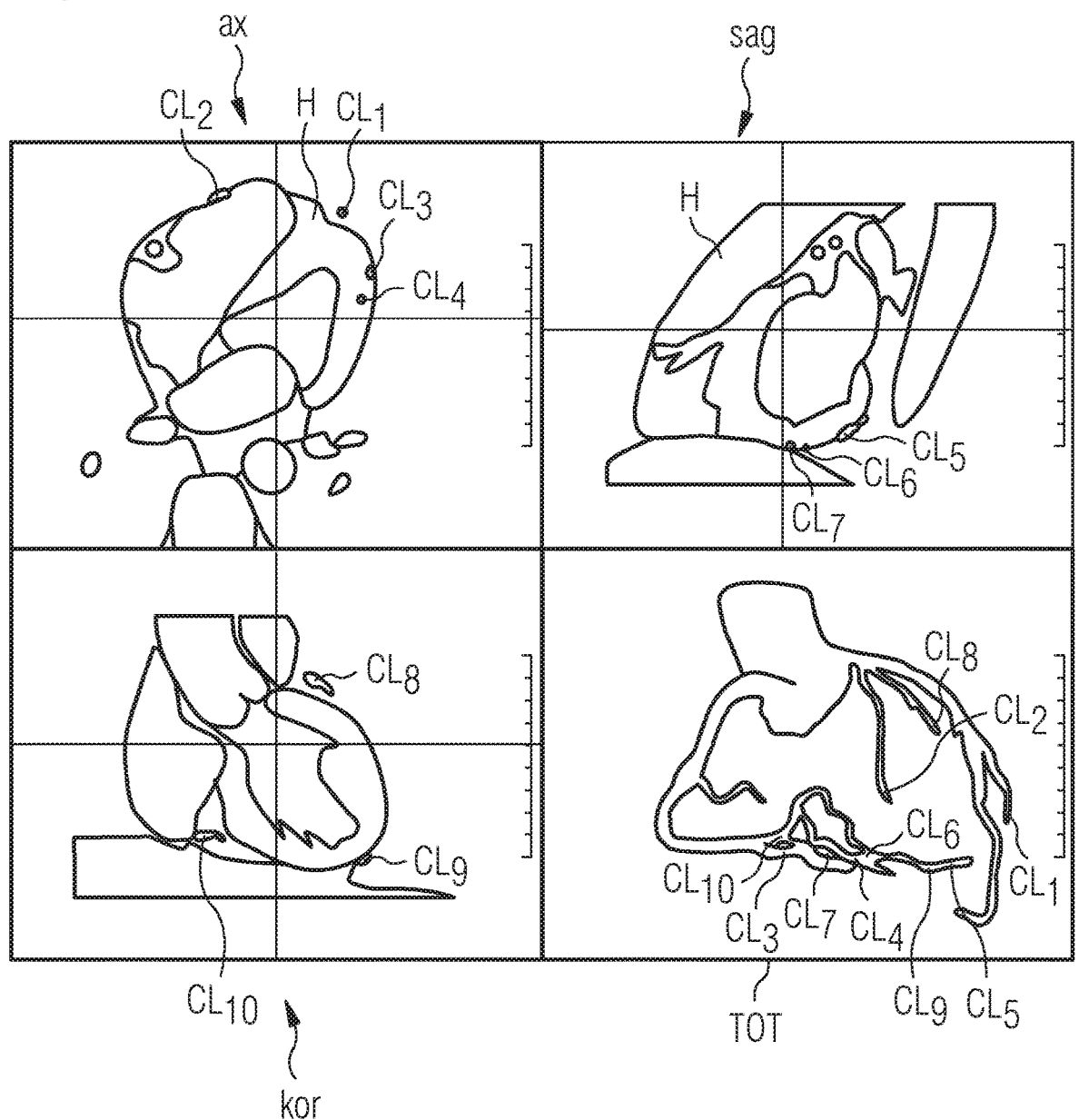
FIG. 2 shows images of a heart which illustrate a specification of centerlines of the coronary blood vessels.

FIG. 2 shows three different two-dimensional sectional views ax, sag, kor of the heart H, plus, in addition, in a detail drawing at bottom right, an overall view TOT of the coronary tree. An axial view of the heart H is shown in a detail drawing ax at top left. In the axial view ax, positions $CL_1$, $CL_2$, $CL_3$, $CL_4$ are determined which are to be regarded as central points of coronary vessels. Similarly, in a detail drawing sag at top right, which shows a sagittal view of the heart H, positions $CL_5$, $CL_6$, $CL_7$ are identified which represent central points of the coronary vessels of the heart. What are to be understood as central points in this context are points on a centerline CL of a vessel. A detail drawing kor at bottom left shows, in a coronal direction, a view of the heart H in which central points $CL_8$, $CL_9$, $CL_{10}$ are in turn marked which likewise belong to blood vessels of the coronary tree of the heart. A perspective view of the coronary tree as a whole is shown in a detail drawing TOT at bottom right. The central points $CL_1, \ldots, CL_{10}$ from the three sectional views ax, sag, kor are also drawn in the coronary tree. Given a correspondingly large number of examined sectional views, centerlines CL of the coronary vessels can therefore be determined by connecting the central points. In the detail drawing TOT at bottom right, vascular structures are actually only "represented" (by suitable windowing and masking) and in fact not modeled geometrically with continuous boundaries according to an embodiment of the invention.

At a step 1.II (see FIG. 1), following the determination of the centerlines CL of the blood vessels of the heart, a two-dimensional view $BD_{2D}$ is generated on the basis of the three-dimensional image data $BD_{3D}$. For this purpose, a so-called non-linear planar reformation or, in this specific case, a curvilinear or curved reformation CPR of the three-dimensional image data $BD_{3D}$ is carried out. Figuratively speaking, a type of mapping of a part of the three-dimensional image data $BD_{3D}$, namely a non-planar surface which comprises the centerlines CL of the coronary vessels, into two-dimensional space is carried out. In this way it is ensured that, in contrast to a multiplanar reformation, the vascular structures around the centerlines are seamlessly imaged also in the two-dimensional view $BD_{2D}$.

Figure 3:
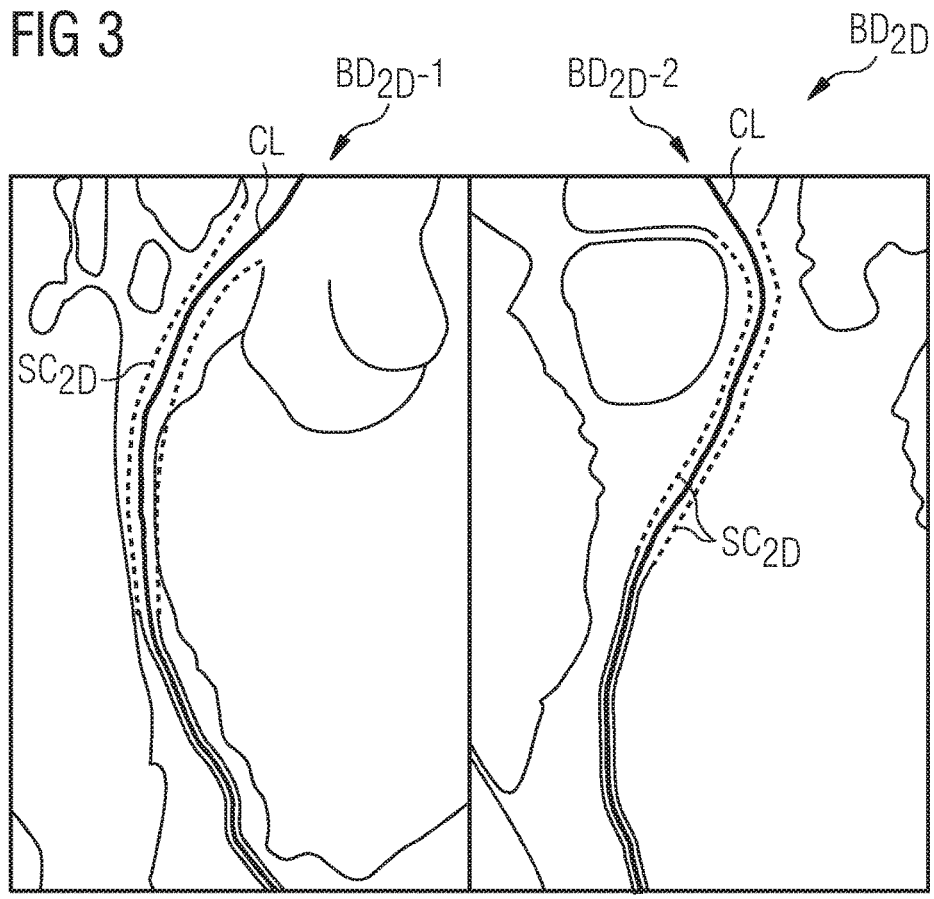
FIG. 3 shows a schematic representation of a step of editing the course of vessel surfaces in a reformatted two-dimensional representation of coronary blood vessels.
Figure 4:
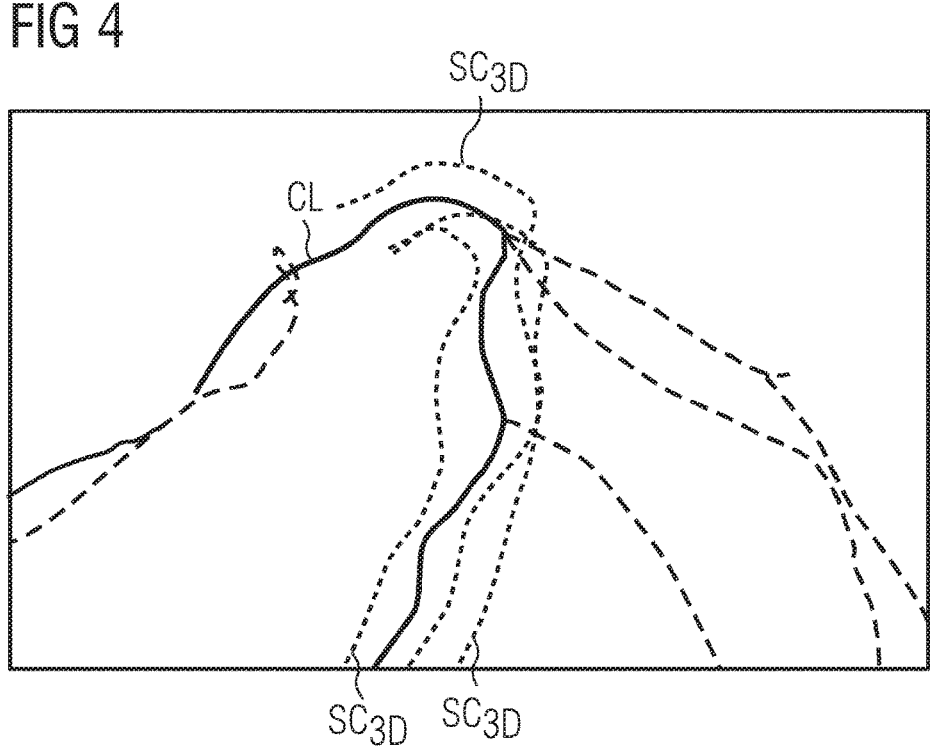
FIG. 4 shows a three-dimensional representation of the course of edited profile lines of the vessel surfaces.

Two such views $BD_{2D}$-1, $BD_{2D}$-2 of vascular structure sections of the heart obtained by way of reformation are shown in FIG. 3. In this case the two images are views rotated through 90° relative to one another. In the first view $BD_{2D}$-1 depicted in FIG. 3, a centerline CL is drawn in which marks the longitudinal course of a coronary vessel. In a view $BD_{2D}$-2 rotated through 90°, a centerline CL of the same coronary vessel is likewise drawn in, this time viewed from a perspective rotated through 90°.

At a step 1.III (see FIG. 1), boundary indicators $SC_{2D}$, in this case boundary lines which mark the actual surface profile of the coronary vessels, are now edited in the two-dimensional view $BD_{2D}$. The marking lines $SC_{2D}$ are likewise drawn in FIG. 3 in the two detail drawings $BD_{2D}$-1, $BD_{2D}$-2. As can be seen in FIG. 3, a "two-dimensional view" $BD_{2D}$ may also comprise a number of such views $BD_{2D}$-1, $BD_{2D}$-2 which illustrate a coronary structure viewed from different directions. The course of the marking lines $SC_{2D}$ may be specified for example by the user on the basis of differences in contrast in the two-dimensional view $BD_{2D}$ and also drawing on his or her knowledge of the anatomy and his or her practical medical experience.

Next, at a step 1.IV, the specified centerlines CL and the marking lines $SC_{2D}$ are back-transformed into three-dimensional space, which entails now applying an inverse transformation compared to the transformation applied in step 1.II. The reformation performed in step 1.II is reversed, so to speak, though in fact only the centerlines CL and the marking lines $SC_{2D}$ are inversely transformed into three-dimensional space in step 1.IV. In step 1.IV, therefore, three-dimensional marking lines $SC_{3D}$ are generated on the basis of the two-dimensional marking lines $SC_{2D}$. If, as illustrated in FIG. 3, two-dimensional views from two different directions are present, then the three-dimensional marking lines $SC_{3D}$ are unequivocally defined by the two-dimensional marking lines $SC_{3D}$ drawn in the two-dimensional views. These marking lines $SC_{3D}$ are illustrated together with centerlines CL in a three-dimensional view in FIG. 4. The marking lines $SC_{3D}$, CL may be used subsequently as sampling points for a modeling of vascular structures COT.

At step 1.V, such a modeling of a coronary vessel section COT is performed on the basis of the three-dimensional marking lines $SC_{3D}$ obtained in step 1.IV as well as on the basis of the centerlines CL already obtained in step 1.I. The modeling may be performed for example as implicit modeling with the aid of radial basis functions, wherein the surface of the vessels is generated in three-dimensional space using an interpolation method. The implicit surfaces obtained in the process may in turn be visualized as explicit surfaces for example by way of three-dimensional surface networks in a three-dimensional view or as intersecting two-dimensional lines in reformatted form in a two-dimensional representation.

Figure 5:
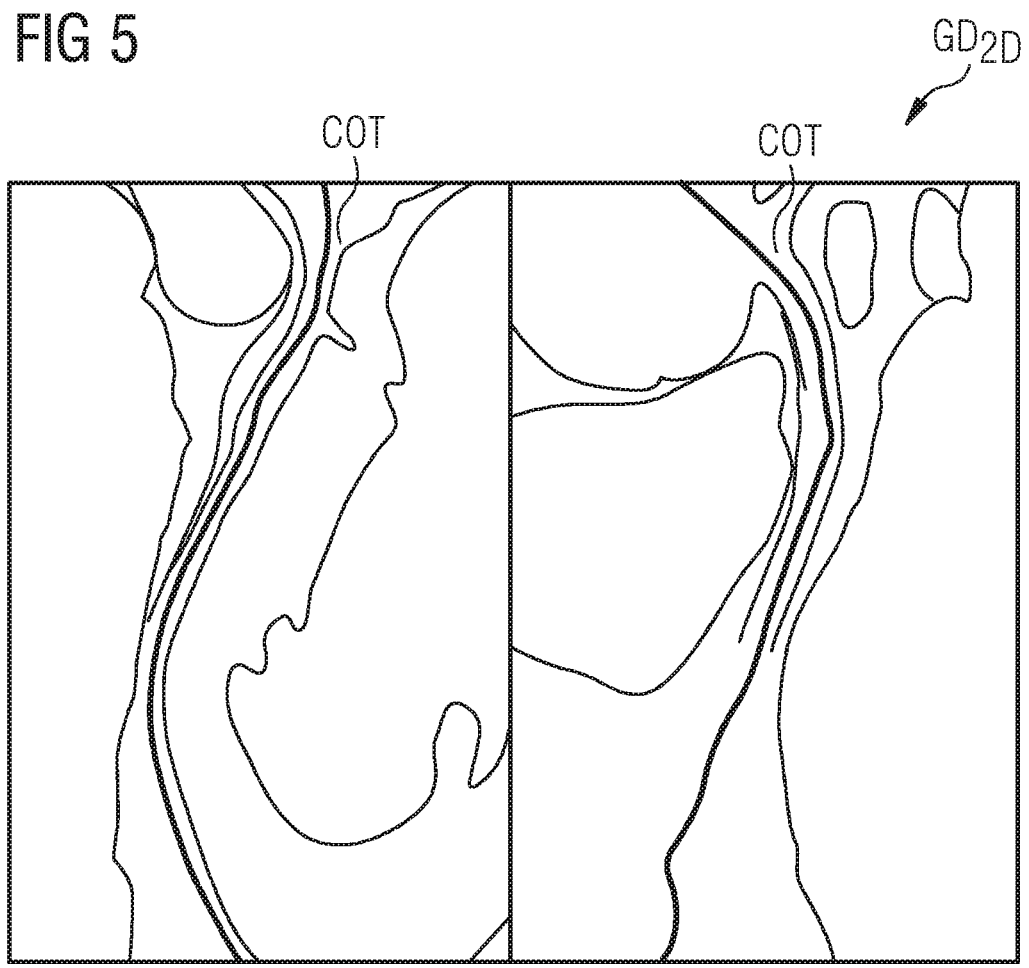
FIG. 5 shows a two-dimensional representation of a modeled vascular structure of a coronary blood vessel.

Such a two-dimensional representation $GD_{2D}$ is shown in FIG. 5, wherein, analogously to FIG. 3, two views of the vascular structures COT, rotated through 90° relative to one another, are depicted. The lines COT representing the vascular structures may also be amended by a user in a correction step and subsequently be back-transformed by inverse reformation into three-dimensional space once again in order to obtain an enhanced model-based representation of the vascular structures COT. This optional procedure is indicated in FIG. 1 by way of a dashed arrow between step 1.V and step 1.III. Subsequently, in step 1.III, new marking lines $SC_{2D}$ can be drawn in to replace the older marking lines. In this case the "inaccurate" older marking lines do not necessarily have to be removed by hand by the user. The older marking lines may, for example, also be transformed as well initially into three-dimensional space in step 1.IV and subsequently an automated sorting process may be performed in which older marking lines lying in a volume region around a new marking line, which volume region is arranged by way of a stack composed of circular ring segments around the centerline at a predetermined angle and at a predetermined distance from the centerline, are discarded. Finally, a modeling of the vascular structures COT is performed once again in step 1.V, this time on the basis of the corrected marking lines.

Figure 6:
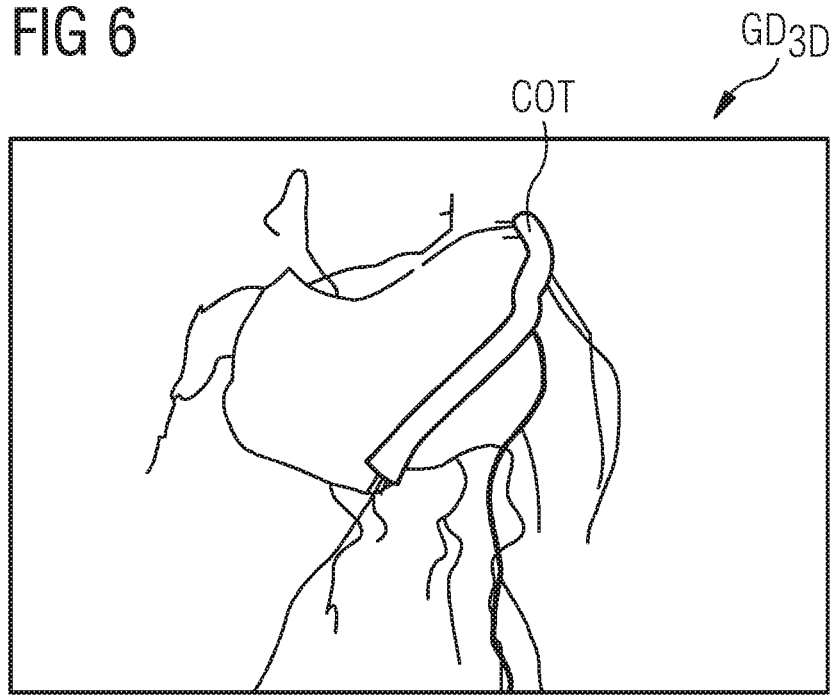
FIG. 6 shows a three-dimensional representation of a modeled coronary blood vessel in a coronary vessel tree.

FIG. 6 shows a three-dimensional view $GD_{3D}$ of a modeled vascular structure COT which is represented by a grid.

Figure 7:
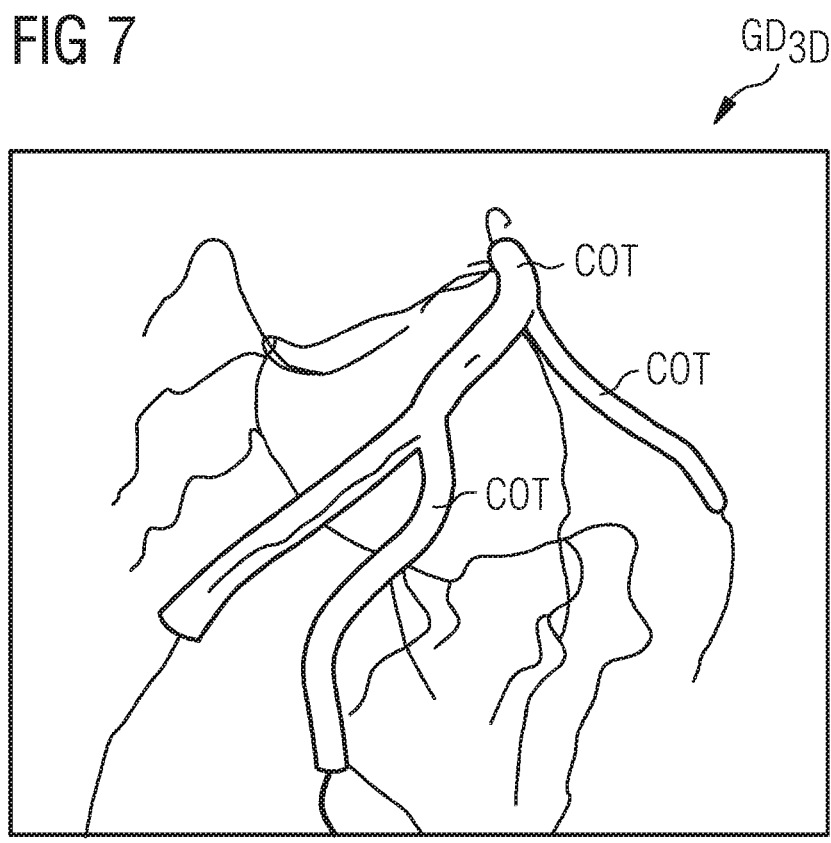
FIG. 7 shows a three-dimensional representation of a plurality of interconnected modeled coronary blood vessels in a coronary vessel tree.

The method described in connection with FIG. 1 to FIG. 6 may be continued with a model-based representation of further vascular sections of the coronary tree that is imaged in the angiography data $BD_{3D}$. Such a continuation of the method is illustrated in FIG. 7, in which further branches COT of the coronary tree are modeled by way of grids. In addition, implicit surfaces which are assigned to different centerlines may also be joined at the transition points between the individual vessel branches, also known as bifurcations. The result of such a general modeling of a larger section of the coronary tree can be seen in FIG. 7.

FIG. 8 shows a block diagram which illustrates a volume object modeling device 80 according to an example embodiment of the invention. The volume object modeling device 80 comprises an input interface 81, which comprises three-dimensional image data $BD_{3D}$ representing an image of the heart. The acquired three-dimensional image data $BD_{3D}$ is transferred to a representation determination unit 82 which determines centerlines CL of the coronary blood vessels on the basis of the three-dimensional image data $BD_{3D}$ and marks the centerlines CL in the three-dimensional image data $BD_{3D}$. The thus marked three-dimensional image data $BD_{3D}$ is transferred to a reformation unit 83, which, on the basis of the determined centerlines CL, generates a two-dimensional view $BD_{2D}$ therefrom using a non-linear planar reformation CPR.

The image data $BD_{2D}$ of a two-dimensional view generated in this way is forwarded to an image evidence editing unit 84. The image evidence editing unit 84 is used for editing boundary indicators $SC_{2D}$, which define the actual surface profile of the vascular structures COT, in the two-dimensional view $BD_{2D}$. For this purpose, the image evidence editing unit 84 is connected to a communication interface 84*b*, via which a user can draw in marking lines as boundary indicators $SC_{2D}$ in the two-dimensional view, which marking lines are then imported by the image evidence editing unit 84. Next, the marking lines $SC_{2D}$ generated interactively by the user or, as the case may be, image data corresponding thereto are transferred to a back-transformation unit 85, which generates a three-dimensional view $SC_{3D}$ of the edited marking lines $SC_{2D}$ by back-transforming the edited marking lines $SC_{2D}$ into three-dimensional space.

The generated data $SC_{3D}$, comprising three-dimensional marking lines, is finally transferred to a modeling unit 86, which models vascular structures COT in three-dimensional space on the basis of the edited marking lines $SC_{3D}$. The image data containing the modeled vascular structures COT is then output via an output interface 87 to other units—such as, for example, an image data storage unit—in order to be displayed to the user on a screen, for example, or in order to serve as a database for a more rigorous analysis for an evaluation of diagnostic findings.

In conclusion it is pointed out once again that the methods and devices described in the foregoing are simply preferred example embodiments of the invention and that the invention may be varied by the person skilled in the art without leaving the scope of the invention, insofar as this is defined by the claims. The invention is not limited to an application in the field of medicine, but rather the invention may also be applied generally to the determination of volume objects on the basis of image data. It is also pointed out for the sake of completeness that the use of the indefinite articles "a" or "an" does not exclude the possibility that the features in question may also be present more than once. Equally, the term "unit" does not rule out the possibility that the same consists of a plurality of components, which if necessary may also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a geometric model-based representation of a volume object based on three-dimensional image data of the volume object, the three-dimensional image data corresponding to an examination region of interest of an examination subject, the method comprising:
   determining a first representation of the volume object based on the three-dimensional image data;
   generating a single two-dimensional representation using a non-linear planar reformation of the volume object based on the first representation;
   determining first boundary indicators defining a surface profile of the volume object in the single two-dimensional representation;
   generating a three-dimensional representation of the first boundary indicators by back-transforming the first boundary indicators from only the single two-dimensional representation into three-dimensional space;

determining the geometric model-based representation of the volume object based on the first boundary indicators in the three-dimensional representation;

updating the single two-dimensional representation to include second boundary indicators;

generating an updated three-dimensional representation of the first and second boundary indicators by back-transforming the first and second boundary indicators from only the updated single two-dimensional representation into three-dimensional space; and determining an updated geometric model-based representation of the volume object based on the first and second boundary indicators including discarding at least one of the first boundary indicators in the updated three-dimensional representation.

2. The method of claim 1, wherein the volume object has a tubular structure.

3. The method of claim 2, wherein the tubular structure comprises a three-dimensional vascular structure.

4. The method of claim 3, wherein the tubular structure comprises a coronary vascular structure.

5. The method of claim 3, wherein the first representation comprises a centerline defining a course of the tubular structure.

6. The method of claim 3, wherein the first boundary indicators correspond to tube walls of the tubular structure.

7. The method of claim 2, wherein the first representation comprises a centerline defining a course of the tubular structure.

8. The method of claim 2, wherein the first boundary indicators correspond to tube walls of the tubular structure.

9. The method of claim 2, wherein the volume object is a hollow organ.

10. The method of claim 2, wherein the back-transforming is based on an inversion of the non-linear planar reformation.

11. The method of claim 2, wherein the discarded at least one of the first boundary indicators contradicts at least one of the second boundary indicators and extends through a region of the volume object around the second boundary indicators.

12. The method of claim 11, wherein the generating the updated three-dimensional representation and the discarding are iteratively performed until all boundary indicators have been determined and all contradictory boundary indicators have been discarded.

13. The method of claim 1, wherein the back-transforming is based on an inversion of the non-linear planar reformation.

14. The method of claim 1, wherein the discarded at least one of the first boundary indicators contradicts at least one of the second boundary indicators and extends through a region of the volume object around the second boundary indicators.

15. The method of claim 14, wherein the generating the updated three-dimensional representation and the discarding are iteratively performed until all boundary indicators have been determined and all contradictory boundary indicators have been discarded.

16. The method of claim 1, wherein the determining the geometric model-based representation comprises an implicit modeling by interpolating one or more surfaces of the volume object with one or more radial basis functions.

17. The method of claim 1, wherein the geometric model-based representation is represented by at least one of a surface network in three-dimensional space, or one or more intersection lines lying on a reformatted surface of the single two-dimensional representation.

18. The method of claim 17, wherein:
the geometric model-based representation is represented by the one or more intersection lines; and
the one or more intersection lines are used as candidate boundary indicators during an iterative process of editing boundary indicators used to refine the geometric model-based representation.

19. The method of claim 1, wherein the single two-dimensional representation is distinct from all planes of the three-dimensional image data.

20. The method of claim 1, wherein the three-dimensional representation is distinct from the three-dimensional image data.

21. A volume object modeling device, comprising:
a representation determination unit configured to determine a first representation of a volume object based on three-dimensional image data;
a reformation unit configured to,
generate a single two-dimensional representation using a non-linear planar reformation of the volume object based on the first representation, and
update the single two-dimensional representation to include second boundary indicators;
an image evidence editing unit configured to determine first boundary indicators defining a surface profile of the volume object in the single two-dimensional representation;
a back-transformation unit configured to,
generate a three-dimensional representation of the first boundary indicators by back-transforming the first boundary indicators from only the single two-dimensional representation into three-dimensional space, and
generate an updated three-dimensional representation of the first and second boundary indicators by back-transforming the first and second boundary indicators from only the updated single two-dimensional representation into three-dimensional space; and
a modeling unit configured to,
generate a model-based representation of the volume object based on the first boundary indicators in the three-dimensional representation, and
generate an updated model-based representation of the volume object based on the first and second boundary indicators including discarding at least one of the first boundary indicators in the updated three-dimensional representation.

22. A medical imaging device, comprising:
a scan unit configured to scan an examination region of interest of a subject to be examined;
a control device configured to control the scan unit; and
the volume object modeling device of claim 21.

23. The medical imaging device of claim 22, wherein the medical imaging device is a CT system.

24. A non-transitory computer-readable medium storing a computer program loadable into a memory device of a control device of a medical imaging device, the computer program including program sections that, when executed by at least one processor of the control device, cause the at least one processor to perform the method of claim 1.

25. A non-transitory computer-readable medium storing program sections, readable and executable by at least one processor, the program sections causing the at least one processor to perform the method of claim 1 when the program sections are executed by the at least one processor.

26. A volume object modeling device, comprising:
    a memory storing executable computer-readable instructions; and
    at least one processor configured to execute the computer-readable instructions to
      determine a first representation of a volume object based on three-dimensional image data,
      generate a single two-dimensional representation using a non-linear planar reformation of the volume object based on the first representation,
      determine first boundary indicators defining a surface profile of the volume object in the single two-dimensional representation,
      generate a three-dimensional representation of the first boundary indicators by back-transforming the first boundary indicators from only the single two-dimensional representation into three-dimensional space,
      generate a model-based representation of the volume object based on the first boundary indicators in the three-dimensional representation,
      update the single two-dimensional representation to include second boundary indicators,
      generate an updated three-dimensional representation of the first and second boundary indicators by back-transforming the first and second boundary indicators from only the updated single two-dimensional representation into three-dimensional space, and
      determine an updated model-based representation of the volume object based on the first and second boundary indicators including discarding at least one of the first boundary indicators in the updated three-dimensional representation.

27. A medical imaging device, comprising:
    a scan unit configured to scan an examination region of interest of a subject to be examined;
    a control device configured to control the scan unit; and
    the volume object modeling device of claim 26.

28. The medical imaging device of claim 27, wherein the medical imaging device is a CT system.

29. A non-transitory computer-readable medium storing a computer program loadable into a memory device of a control device of a medical imaging device, the computer program including program sections that, when executed by at least one processor of the control device, cause the at least one processor to perform the method of claim 2.

30. A non-transitory computer-readable medium storing program sections, readable and executable by at least one processor, the program sections causing the at least one processor to perform the method of claim 2 when the program sections are executed by the at least one processor.

* * * * *